United States Patent [19]
Häfele et al.

[11] Patent Number: 5,658,445
[45] Date of Patent: Aug. 19, 1997

[54] COMBINATION OF LAMBDA PROBES

[76] Inventors: Edelbert Häfele, Albert-Einstein-Strasse 62, D-76228 Karlsruhe; Ulrich Schönauer, Sternbergstrasse 1, D-76131 Karlsruhe; Jörg Huber, Franz-Lehar-Weg 4, D-76448 Durmersheim, all of Germany

[21] Appl. No.: 507,462

[22] PCT Filed: Feb. 9, 1994

[86] PCT No.: PCT/EP94/00370

§ 371 Date: Aug. 28, 1995

§ 102(e) Date: Aug. 28, 1995

[87] PCT Pub. No.: WO94/19593

PCT Pub. Date: Sep. 1, 1994

[30] Foreign Application Priority Data

Feb. 26, 1993 [DE] Germany ............... 43 06 035.8
Jun. 23, 1993 [DE] Germany ............... 43 20 881.9

[51] Int. Cl.$^6$ ..................................... G01H 27/26
[52] U.S. Cl. ..................... 204/425; 204/426; 204/427; 422/94; 422/97; 422/98; 123/672; 123/674; 123/693; 123/697

[58] Field of Search .................. 123/672, 673, 123/674, 676, 693, 697; 204/425, 426, 427; 422/94, 97, 98

[56] References Cited

FOREIGN PATENT DOCUMENTS

| 2216016 | 8/1974 | France . |
|---|---|---|
| 57-203843 | 12/1982 | Japan . |
| 60-231159 | 11/1985 | Japan . |
| 61-083466 | 4/1986 | Japan . |
| 61-155751 | 7/1986 | Japan . |
| 2054211 | 2/1981 | United Kingdom . |

*Primary Examiner*—Bruce F. Bell
*Attorney, Agent, or Firm*—Antonelli, Terry, Stout & Kraus, LLP.

[57] ABSTRACT

The invention relates to a combination of a heated lambda sensor with a stepped or binary sensor characteristic and another heated lambda sensor to determine the lambda value in a gas mixture, e.g. in the exhaust gas preferably of internal combustion engines, the output signal from one lambda sensor being used to calibrate the other one, and the two lambda sensors are arranged closely beside each other, the other lambda sensor having a wide-baud sensor characteristic.

16 Claims, 2 Drawing Sheets

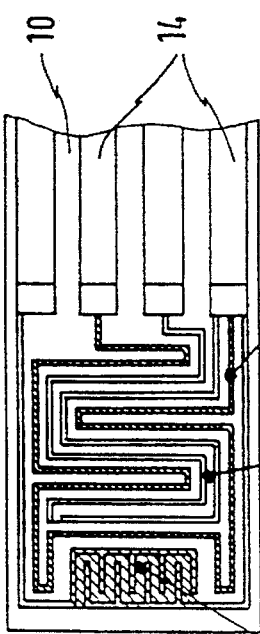
FIG. 1
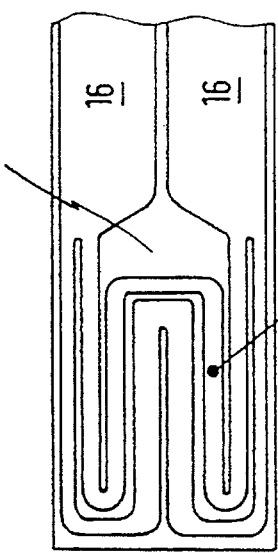
FIG. 2
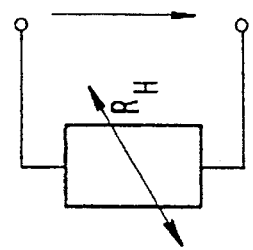
FIG. 6
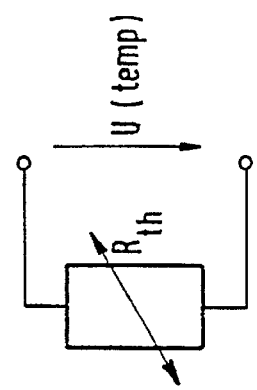
FIG. 5
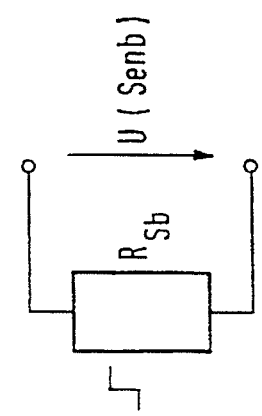
FIG. 4
FIG. 3

COMBINATION OF LAMBDA PROBES

BACKGROUND OF THE INVENTION

1. Field of the Invention

This application is a 371 of PCT/EP94/00370 published Feb. 9, 1994.

The invention relates to a combination of a heated lambda probe with an abrupt or binary sensor characteristic and an additional heated lambda probe for determining the lambda value in a gas mixture, for example in exhaust, preferably from internal combustion engines.

2. Description of the Prior Art

Lambda probes are known (DE-A-41 09 560) and operate as binary lambda probes which merely determine whether the value above or below the lambda value is equal to one.

Since known lambda probes are subject to drift, i.e. the measured lambda values change during operation or as a result of aging, two-probe systems are known (DE-OS 24 44 334, DE-OS 223 04 622, U.S. Patent No. 4,739,614).

In addition, a combination composed of two probes is known (DE-A0-41 35 254), in which one probe is located upstream of the catalyst itself and the other is located beyond the catalyst in the flow direction, with one of the two probes serving to detect changes in the measurement behavior of the other and to compensate for them.

In the known combination composed of two lambda probes, however, errors occur because of the considerable distances between the two lambda probes.

SUMMARY OF THE INVENTION

The object of the invention is to improve the accuracy of the values measured by the known probe despite the drift that occurs.

According to the invention, therefore, the binary lambda probe, which undergoes a change in resistance at a lambda value of 1, and a second broadband lambda probe are located in direct proximity with one another. By this combination, the broadband lambda probe can be calibrated with the aid of a binary probe at a lambda value=1 in such fashion that the broadband lambda probe is calibrated for drift. It exhibits a broadband constantly changing resistance which is preferably linear in the range from lambda 0.8 to lambda 1.2. As a result of the high accuracy of the determination of the value of lambda in the vicinity of lambda=1, improved regulation of a motor, especially in dynamic operating states, can be achieved. The required high accuracy within a small measurement range can be achieved with the aid of the additional lambda probe used according to the invention. Oxygen-sensitive materials, one with an abrupt and the other with a broadband sensor characteristic, are applied to one sensor element, preferably in immediate proximity to one another, or to a common substrate which has the same temperature. The abrupt signal can be used to calibrate the broad band probe, which is preferably temperature regulated, exactly in every operating state. In addition, very rapid temperature fluctuations in the exhaust that usually cause error in the sensor signal when both sensor elements are on a common substrate with the same temperature, are compensated by the substrate being heated. In addition, as a result of their immediate proximity to one another, practically identical gas is measured in the gas mixture that would otherwise be concentrated differently over the flow range. Likewise it is possible to vary the working temperature on the common substrate to compensate for drift.

BRIEF DESCRIPTION OF THE DRAWINGS

One embodiment of the invention will now be described in greater detail with reference to the drawing.

FIG. 1 shows two lambda probes on a substrate, in a top view;

FIG. 2 shows the substrate according to FIG. 1 in a top view;

FIGS. 3–6 show equivalent resistance diagrams of the components on the substrate according to FIGS. 1 and 2;

FIG. 1 shows substrate 10 in a top view in a schematic and partially cutaway form. A first broadband lambda probe 11 of known construction, a binary lambda probe 12, and a temperature sensor 13 are provided in a known manner in laminating technology using screen printing, and are connected by a total of terminal leads 14 that are also formed by a thick layer technology as conducting strips applied to the substrate.

Figure 7:
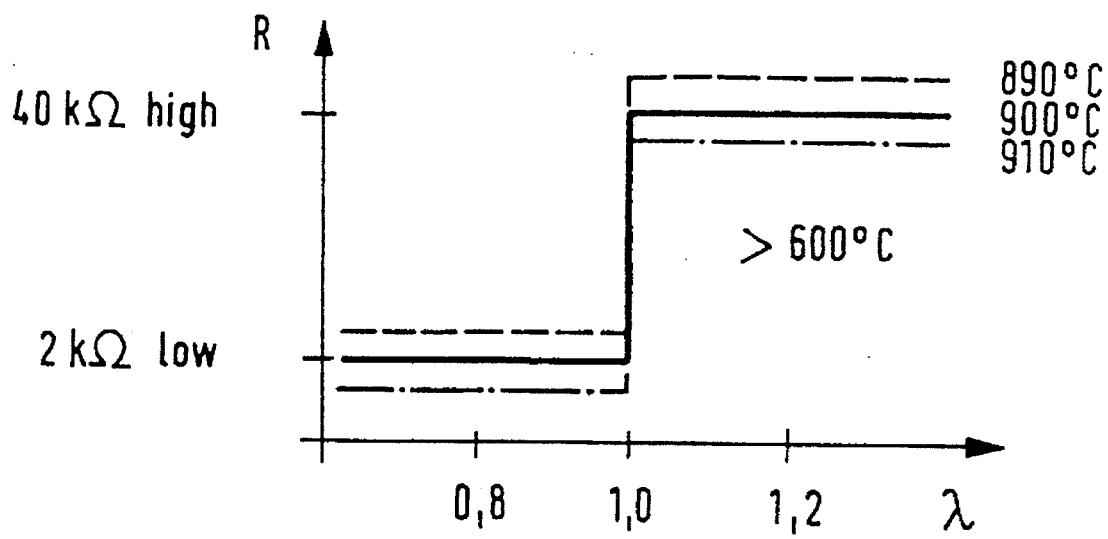
FIG. 7 shows a resistance diagram showing the lambda value of the binary lambda probe.

On the back (FIG. 2) of substrate 10 a resistance heating layer 15 is provided that is connectable by two connecting contact strips 16 to an electrical voltage source.

In this way, the electrical behavior of the two lambda probes, 11, 12 of temperature sensor 13 as well as that of sensor heater 15 can be represented as electrical resistances in the equivalent circuit diagram as shown in FIGS. 3 to 6. the temperature sensor is used to calibrate the first broadband probe 11

Figure 8:
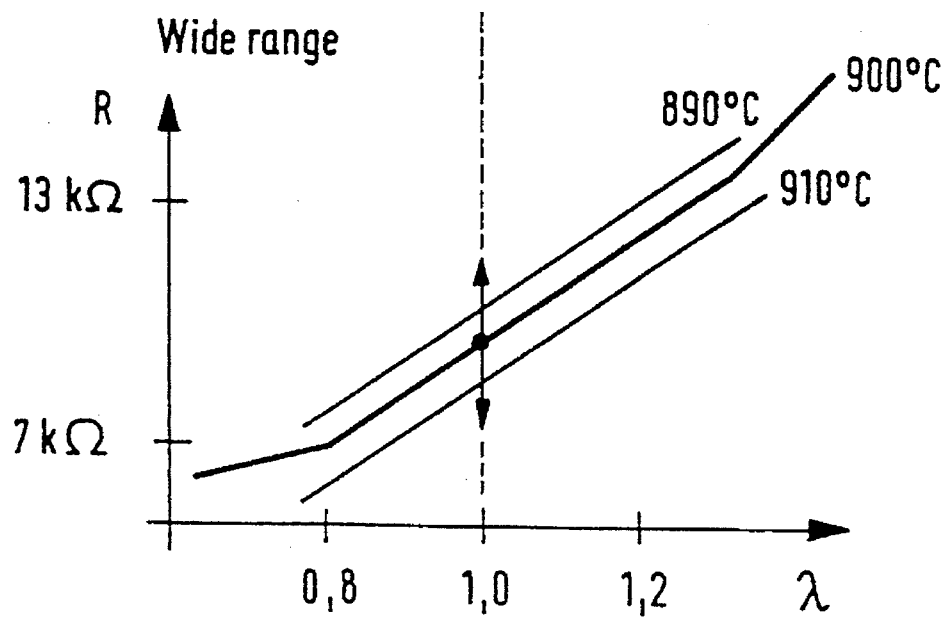
FIG. 8 is a resistance diagram showing the lambda value of the broadband lambda probe with a family of curves.

FIG. 8 also shows a family of curves for electrical resistance versus lambda value for different operating temperatures, namely 890° C., 900° C., and 910° C. of the first broadband lambda probe. It is evident that as the temperature rises, the resistance for a given value of lambda falls. It is also evident that the individual curves are approximately linear in the range from 0.8<lambda<1.2.

On the other hand, the binary abrupt lambda probe, whose resistance equivalent diagram appears in FIG. 7, changes abruptly and is shown for a single operating temperature.

We claim:

1. An apparatus for determining a lambda value in a gas mixture in an exhaust comprising:

a substrate containing a first lambda probe having a binary sensor characteristic and a second lambda probe and a heater for heating the first and second lambda probes to a common temperature and means responsive to an output signal from the first lambda probe for calibrating the second lambda probe.

2. An apparatus in accordance with claim 1, wherein:

the second lambda probe has a broadband characteristic.

3. An apparatus in accordance with claim 2, wherein:

the broadband characteristic is linear in a range which extends from below lambda equaling one to above lambda equaling one; and the binary sensor characteristic changes in resistance at lambda equaling one from a lower resistance to a higher resistance.

4. An apparatus in accordance with claim 3, wherein: the linear range extends from lambda equaling 0.8 to lambda equaling 1.2; and the resistance changes at lambda equaling one from two thousand ohms to forty thousand ohms.

5. An apparatus in accordance with claim 4, wherein:

the substrate further comprises a temperature sensor for calibrating the second lambda probe.

6. An apparatus in accordance with claim 5, wherein:

the first and second lambda probes are disposed on a first side of the substrate and the heater is a layer disposed on a second side of the substrate.

7. An apparatus in accordance with claim 4, wherein:

the first and second lambda probes are disposed on a first side of the substrate and the heater is a layer disposed on a second side of the substrate.

8. An apparatus in accordance with claim 3, wherein:

the substrate further comprises a temperature sensor for calibrating the second lambda probe.

9. An apparatus in accordance with claim 8, wherein:

the first and second lambda probes are disposed on a first side of the substrate and the heater is a layer disposed on a second side of the substrate.

10. An apparatus in accordance with claim 3, wherein:

the first and second lambda probes are disposed on a first side of the substrate and the heater is a layer disposed on a second side of the substrate.

11. An apparatus in accordance with claim 2, wherein:

the substrate further comprises a temperature sensor for calibrating the second lambda probe.

12. An apparatus in accordance with claim 11, wherein:

the first and second lambda probes are disposed on a first side of the substrate and the heater is a layer disposed on a second side of the substrate.

13. An apparatus in accordance with claim 2, wherein:

the first and second lambda probes are disposed on a first side of the substrate and the heater is a layer disposed on a second side of the substrate.

14. An apparatus in accordance with claim 1, wherein:

the substrate further comprises a temperature sensor for calibrating the second lambda probe.

15. An apparatus in accordance with claim 14, wherein:

the first and second lambda probes are disposed on a first side of the substrate and the heater is a layer disposed on a second side of the substrate.

16. An apparatus in accordance with claim 1, wherein:

the first and second lambda probes are disposed on a first side of the substrate and the heater is a layer disposed on a second side of the substrate.

* * * * *